(12) United States Patent
Gutowska

(10) Patent No.: US 6,979,464 B2
(45) Date of Patent: *Dec. 27, 2005

(54) REVERSIBLE GELING CO-POLYMER AND METHOD OF MAKING

(75) Inventor: Anna Gutowska, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/209,541

(22) Filed: Dec. 11, 1998

(65) Prior Publication Data

US 2003/0096010 A1 May 22, 2003

Related U.S. Application Data

(63) Continuation-in-part of application No. 08/870,368, filed on Jun. 6, 1997, now abandoned.

(51) Int. Cl.$^7$ ............................................... A61K 9/14
(52) U.S. Cl. ...................... 424/484; 525/54.2; 525/54.3; 525/54.1; 424/488
(58) Field of Search ................................. 424/484, 488; 525/54.2, 54.3, 54.1

(56) References Cited

U.S. PATENT DOCUMENTS

| | | |
|---|---|---|
| 4,147,764 A | 4/1979 | Levy et al. |
| 4,526,938 A | 7/1985 | Churchill et al. |
| 4,732,930 A | 3/1988 | Tanaka et al. |
| 5,000,955 A | 3/1991 | Gould et al. |
| 5,053,228 A | 10/1991 | Mori et al. |
| 5,124,151 A | 6/1992 | Viegas et al. |
| 5,226,902 A | 7/1993 | Bae et al. |
| 5,252,318 A | 10/1993 | Joshi et al. |
| 5,262,055 A | 11/1993 | Bae et al. ................... 210/645 |
| 5,278,201 A | 1/1994 | Dunn et al. |
| 5,290,494 A | 3/1994 | Coombes et al. |
| 5,292,517 A | 3/1994 | Chang |
| 5,410,016 A | 4/1995 | Hubbell et al. |
| 5,441,732 A | 8/1995 | Hoeg et al. ............... 424/78.04 |
| 5,449,513 A | 9/1995 | Yokoyama et al. |
| 5,462,990 A | 10/1995 | Hubbell et al. |
| 5,484,610 A | 1/1996 | Bae |
| 5,514,379 A | 5/1996 | Weissleder et al. |
| 5,525,334 A | 6/1996 | Ito et al. |
| 5,575,815 A | 11/1996 | Slepian et al. |
| 5,580,929 A | 12/1996 | Tanaka et al. |
| 5,624,685 A | 4/1997 | Takahashi et al. |
| 5,631,337 A | 5/1997 | Sassi et al. |
| 5,634,946 A | 6/1997 | Slepian |
| 5,643,246 A | 7/1997 | Leeb et al. |
| 5,702,717 A | 12/1997 | Cha et al. |
| 5,752,974 A | 5/1998 | Rhee et al. |
| 5,788,687 A | 8/1998 | Batich et al. |
| 5,820,879 A | 10/1998 | Fernandez et al. |
| 5,843,156 A | 12/1998 | Slepian et al. |
| 5,843,331 A | 12/1998 | Schober et al. |
| 5,858,746 A | 1/1999 | Hubbell et al. |
| 5,876,741 A | 3/1999 | Ron |
| 5,939,485 A | 8/1999 | Bromberg et al. |
| 5,942,209 A | 8/1999 | Leavitt et al. ............. 424/1.25 |
| 5,954,706 A | 9/1999 | Sahatjian |
| 5,969,052 A | 10/1999 | Mumick et al. |
| 5,976,648 A | 11/1999 | Li et al. |
| 5,998,588 A | 12/1999 | Hoffman et al. |
| 6,015,541 A | 1/2000 | Greff et al. ................ 424/1.25 |
| 6,030,634 A | 2/2000 | Wu et al. |
| 6,060,582 A | 5/2000 | Hubbell et al. |
| 6,065,572 A | 5/2000 | Schober et al. |
| 6,083,524 A | 7/2000 | Sawhney et al. |
| 6,290,729 B1 | 9/2001 | Slepian et al. |
| 6,296,831 B1 * | 10/2001 | Weller et al. .............. 424/1.29 |
| 6,352,682 B2 | 3/2002 | Leavitt et al. |
| 6,417,247 B1 * | 7/2002 | Armstrong et al. ......... 523/115 |
| 6,486,213 B1 | 11/2002 | Chen et al. |
| 6,734,147 B2 * | 5/2004 | Levy .......................... 508/103 |
| 6,869,588 B2 * | 3/2005 | Weller et al. .............. 424/1.29 |
| 2001/0046518 A1 | 11/2001 | Sawhney |

FOREIGN PATENT DOCUMENTS

| | | |
|---|---|---|
| EP | 0 534 015 A1 | 9/1991 |
| EP | 534015 | 3/1993 |
| EP | 0 704 217 A2 | 4/1996 |
| JP | 06-293632 | 10/1994 |
| WO | PCT/US91/04104 | 6/1990 |
| WO | PCT/US91/01884 | 3/1991 |
| WO | WO 91/15526 A2 | 10/1991 |
| WO | WO 91/19481 A1 | 12/1991 |
| WO | WO 95/00162 A1 | 1/1995 |
| WO | WO 95/07719 A1 | 3/1995 |
| WO | WO 95/24430 A2 | 9/1995 |
| WO | WO 96/03112 A1 | 2/1996 |
| WO | PCT/US96/10376 | 6/1996 |
| WO | WO 97/00275 A2 | 1/1997 |
| WO | WO 97/09068 A2 | 3/1997 |
| WO | WO 99/07343 A1 | 2/1999 |
| WO | WO 99/49908 A1 | 10/1999 |
| WO | WO 99/55386 A2 | 11/1999 |
| WO | WO 00/07603 A2 | 2/2000 |

OTHER PUBLICATIONS

PH Sensitive Hydrogels Based on Thermally Reversible Gels for Enteric Drug Delivery, LC Dong, AS Hoffman, P Sadumi, Proceed. Intern. Symp. Control. Rel. Vioac. M., 18, (1989), Controlled Release Society, P 95–96.

(Continued)

Primary Examiner—Jeffrey Mullis
(74) Attorney, Agent, or Firm—Klarquist Sparkman, LLP

(57) ABSTRACT

The present invention is a thereapeutic agent carrier having a thermally reversible gel or geling copolymer that is a linear random copolymer of an [meth-]acrylamide derivative and a hydrophilic comonomer, wherein the linear random copolymer is in the form of a plurality of linear chains having a plurality of molecular weights greater than or equal to a minimum geling molecular weight cutoff and a therapeutic agent.

6 Claims, 3 Drawing Sheets

OTHER PUBLICATIONS

Lower Critical Solution Temperatures of Aqueous Copolymers of N–Isopropylacrylamide and Other N–Substituted Acrylamides, JH Priest, SI Murray, RJ Nelson, AS Hoffman, Reversible Polymeric Gels and Related Systems, Chapter 18, American Chemical Society, 1987.

Development if Injectable Sustained–Release Gels for Site–Specific Treatment of Solid Tumors and *Condylomata acuminata,* R. Jones, 6th Int. Symp. on Recent Advances in Drug Delivery Systems, Feb. 22–25, 1193, SLC, UT.

Graft Copolymers that Exhibit Temperature–Induced Phase Transitions Over a Wide Range of PH, G Chen, AS Hoffman, Letters to Nature, Nature vol. 373, Jan. 5, 1995, P 49–52.

Inverse Thermally–Reversible Gelation of Aqueous N–Isopropylacrylamide Copolymer Solutions, CK Han, YH Bae, Polymer, vol. 39, No. 13, pp. 2809–2814, 1998.

Thermally Reversible Polymer Gels for Biohybrid Artificial Pancreas, B Vernon, Macromol. Symp., vol. 9, pp. 155–167, 1996.

Bae et al., "Temperature Dependence of Swelling of Crosslinked Poly(N,N'-alkyl substituted acrylamides) in Water," Journal of Polymer Science: Part B: Polymer Physics, vol. 28, p. 923–936, 1990.

Beltran et al., "Swelling Equilibria for Weakly Ionizable, Temperature–Sensitive Hydrogels," Macromolecules, vol. 24, p. 549–551, 1991.

Brazel et al., "Temperature– and pH– Sensitive Hydrogels for Controlled Release of Antithrombotic Agents," Materials Research Society Symposium Proceedings, vol. 331, p. 211–216, 1994.

Chen et al., "A New Temperature– and pH–Responsive Copolymer for Possible Use in Protein Conjugation," Macromolecular Chemistry and Physics, vol. 196, p. 1251–1259, 1995.

Feil et al., "Effect of Comonomer Hydrophilicity and Ionization on the Lower Critical Solution Temperature of N–Isopropylacrylamide Copolymers," Macromolecules, vol. 26, p. 2496–2500, 1993.

Gutowska et al., "Thermosensitive Polymers for Drug Delivery," Polymer Preprints (American Chemical Society, Division of Polymer Chemistry), vol. 37, No. 2, p. 115–116, 1996.

Hoffman et al., "Conjugates of Stimuli–Responsive Polymers and Biomolecules," Macromolecular Symposia, vol. 118, p. 553–563, 1997.

Hoffman, "Intelligent Polymers in Medicine and Biotechnology," Artificial Organs, vol. 19, No. 5, p. 458–467, May 1995.

Hoffman, "Environmentally Sensitive Polymers and Hydrogels," MSR Bulletin, vol. 16, No. 9, p. 42–46, Sep. 1991.

Jeong et al., "Biodegradable Block Copolymers as Injectable Drug–Delivery Systems," Nature, vol. 388, No. 6645, p. 860–862, Aug. 1997.

Okano et al., "Temperature–Responsive Poly(N–Isopropylacrylamide) as a Modulator for Alteration of Hydrophilic/Hydrophobic Surface Properties to Control Activation/Inactivation of Platelets," Journal of Controlled Release, vol. 36, p. 125–133, 1995.

Park et al., "Effect of Temperature Cycling on the Activity and Productivity of Immobilized β–Galactosidase in a Thermally Reversible Hydrogel Bead Reactor," Applied Biochemistry and Biotechnology, vol. 19, p. 1–9, 1988.

Park et al., "Immobilization and Characterization of β–Galactosidase in Thermally Reversible Hydrogel Beads," Journal of Biomedical Materials Research, vol. 24, p. 21–38, 1990.

Takei et al., "Temperature–Modulated Platelet and Lymphocyte Interactions with Poly(N–Isopropylacrylamide)–Grafted Surfaces," Biomaterials, vol. 16, No. 9, pp. 667–673, 1995.

Vernon et al., "In Vitro Insulin Release of Rat Islets Entrapped in Thermally Reversible Polymer Gel," Proceedings of the International Symposium on Controlled Release of Bioactive Materials, 23rd, p. 216–217, 1996.

Yan et al., "Polymer Communications," Polymer, vol. 36, No. 4, p. 887–889, 1995.

Park et al., "Synthesis, Characterization, and Application of pH/Temperature–Sensitive Hydrogels," *Proceed. Intern. Symp. Control. Rel. Bioact. Mater.*, vol. 17, pp. 112–113, 1990.

Vakkalanka et al., "Temperature–and pH–Sensitive Terpolymers for Modulated Delivery of Streptokinase," *J. Biomater. Sci. Polymer Edn.*, vol. 8, No. 2, pp. 119–129, 1996.

* cited by examiner

US 6,979,464 B2

REVERSIBLE GELING CO-POLYMER AND METHOD OF MAKING

This application is a Continuation-In-Part of application Ser. No. 08/870,368 filed Jun. 6, 1997, now abandoned.

This invention was made with Government support under Contract DE-AC06 76RLO 1830 awarded by the U.S. Department of Energy. The Government has certain rights in the invention.

FIELD OF THE INVENTION

The present invention relates generally to a reversible gel and method of making same. More specifically, the gel is a random copolymer of an [meth-]acrylamide derivative with a hydrophilic comonomer.

As used herein, the term [meth-]acrylamide denotes methacrylamide, acrylamide, or combinations thereof.

As used herein, the chemical prefix "N-" denotes "N-" "N,N-", or combinations thereof. For example N-akyl substituted (meth-) acrylamide means N-akyl substituted (meth-) acrylamide, N,N-akyl substituted (meth-) acrylamide, or combinations thereof.

BACKGROUND OF THE INVENTION

Stimuli-sensitive reversible hydrogels are herein defined as copolymer-solvent systems that undergo a transition between a solution and a gel state in response to the external stimuli such as temperature, pH, ionic strength, solvent composition, sheer stress or a combination of these factors. A reversible stimuli-sensitive gel is one in which the transition is reversed upon reversal of the stimulus. A well known example of a reversible hydrogel is an aqueous solution of gelatin that is in a solution state at high temperatures (e.g. 80° C.) and forms a gel at lower temperatures (e.g., 20° C.). Other examples of reversible gels involve aqueous solutions of agarose and kappa-carrageenan that gel in response to the temperature change, and aqueous solutions of alginate that gel in response to the increased concentration of calcium ions. Reversible hydrogel systems are used in food and pharmaceutical industries as thickeners and suspending agents.

Some specific reversible geling copolymers were also investigated as drug delivery systems and tissue engineering polymer matrices. High viscosity aqueous solutions containing 20 (or more) wt. % of block copolymers of polyethylene oxide and polypropylene oxide, e.g. Poloxamer 407 and Pluronic F68 (Poloxamer 188) exhibit reverse thermal gelation. Solutions of Poloxamer 407 have been investigated for intraocular administration. Solutions containing 25 and 30 wt % of Poloxamer 407 have been prepared and the force needed to inject them through a 25 GA needle was investigated. It was concluded that a liquid-gel transition occurred inside the needle, due to the heat transfer between the needle walls and the surroundings. [J. Juhasz, A. Cabana, A. Ait-Kadi, EVALUATION OF THE INJECTION FORCE OF POLOXAMER 407 GELS FOR INTRAOCULAR ADMINISTRATION, Pharm. Res., 13, No. 9, 1996, Symposium Supplement, S-276].

In another example, 25 wt. % aqueous solution of Pluronic F68 was mixed with articular chondrocyte cells suspension at 4° C. and injected subcutaneously in nude and immunocompetent rabbit. In both cases, the cells entrapped in the copolymer formed tissue with histological appearance of hyaline cartilage. It was concluded that thermally reversible Pluronic F68 gel can serve as an effective injectable matrix for tissue engineering. [C. A. Vacanti, et al., Proceedings of Tissue Engineering Society, Orlando, Fla., 1996]

An example of a pH-reversible hydrogel, investigated as an in situ geling system for ophthalmic use is the aqueous solution of, a poly(acrylic acid)polymer, which undergoes a pH-mediated phase transition at concentrations above 0.1 wt. %. The solution also contains hydroxypropyl methylcellulose, a viscosity enhancing agent. [Pharm. Res., 13, No. 9, 1996, Symposium Supplement].

A new vehicle for topical and mucosal delivery, based on reversible gelation, was developed as an interpenetrating polymer network (IPN) of poly(acrylic acid) and a block copolymer of poly(ethylene oxide)/poly(propylene oxide). When heated from ambient to body temperature the network exhibited a significant viscosity increase from a viscous liquid to a gel-like consistency. It was concluded that at higher temperature, reduced release rates of active ingredients from the network were observed due to the increased viscosity of the IPN. [E. S. Ron, et al., A NEW VEHICLE FOR TOPICAL AND MUCOSAL DRUG DELIVERY, Pharm. Res., 13, No. 9, 1996, Symposium Supplement, S-299].

All gels containing the copolymers of poly(ethylene oxide)/poly(propylene oxide), i.e., Poloxamer 407, Pluronic F68 (Poloxamer 188), an IPN of poly(acrylic acid) and a block copolymer of poly(ethylene oxide)/poly(propylene oxide), and combinations thereof exhibit a limited, concentration dependent, stability of the gel state. The gels formed from these copolymers become liquids upon dilution (as for example due to the dilution with body fluids after peritoneal injection). Additionally, all the above examples of reversible hydrogels exhibit high initial viscosity in a liquid state, i.e., before the geling transition.

Accordingly there is a need for a reversible gel that only reverses when a specific stimulus is reversed and does not reverse upon introduction of a different stimulus (e.g. dilution). Moreover, there is a need for a reversible gel that has a lower initial viscosity.

The U.S. Pat. No. 5,262,055 to Bae et al. discusses an artificial pancreas utilizing reversible gels based on NiPAAM and its copolymers. These polymers and copolymers do not reverse upon dilution and they have a lower initial viscosity. However, the NiPAAM homopolymer described in Example 1 of Bae et al. forms a dense gel with minimal water content (i.e. exhibits substantial syneresis).

Accordingly, there remains a need for a thermally reversible gel without substantial syneresis.

Polymers exhibiting phase transitions in water have many potential uses for drug delivery as stated in GRAFT COPOLYMERS THAT EXHIBIT TEMPERATURE-INDUCED PHASE TRANSITIONS OVER A WIDE RANGE OF pH, G. Chen, AS Hoffman, Nature, Vol 373, 5 Jan. 1995 (pp49–52). In this paper, the authors further describe a temperature sensitive polymer that phase separates with a change in temperature or pH. Chen and Hoffman use graft copolymers having side chains of a temperature sensitive homopolymer, the oligo-N-isopropylacrylamide, grafted onto a pH sensitive homopolymer of acrylic acid. The authors describe the phase separation of the graft copolymer investigated by a cloud point determination in dilute solutions. However, a dilute solution cannot produce a reversible gelation of these graft copolymers. Chen and Hoffman also mention random copolymers of N-isopropylacrylamide and acrylic acid as exhibiting a phase separation, however, there is no description of the intention to study the possibility of reversible gelation in more concentrated solutions of these random copolymers.

The reversible gel of the present invention is useful as a therapeutic agent carrier, for example chemo-embolic material. Chemo-embolic materials are used in treatment of unresectable liver malignancies by a procedure called transcatheter arterial chemo-embolization. The aim of this procedure is to provide therapeutic embolization of the proper hepatic artery and localize the delivery of chemoterapeutic agents. Currently, the procedure is conducted using iodized oil and small pieces of gelatin foam. These materials are not efficient and research continues for finding new materials for chemo-embolization. Accordingly, there is a need for improved chemo-embolization material(s).

SUMMARY OF THE INVENTION

The present invention is a thermally reversible gel or thermally reversible geling copolymer that is a random copolymer of an [meth-]acrylamide derivative and a hydrophilic comonomer, wherein the random copolymer is in the form of a plurality of linear chains having a plurality of molecular weights greater than or equal to a minimum geling molecular weight cutoff. The thermally reversible geling copolymer is enhanced by either combining it with a therapeutic agent in an aqueous solution containing the thermally reversible geling copolymer, and/or by grafting the thermally reversible gelling copolymer to a biodegradable polymer.

The method of the present invention for making a thermally reversible geling copolymer has the steps of:
 (a) mixing an [meth-]acrylamide derivative with a hydrophilic comonomer in a solvent with an initiator forming a reaction mixture;
 (b) polymerizing the reaction mixture and forming a first random copolymer having a plurality of linear chains having a plurality of molecular weights; and
 (c) purifying the polymerized first random copolymer and obtaining a second random copolymer having a plurality of molecular weights greater than or equal to a minimum geling molecular weight cutoff. The method has the further steps of combining the thermally reversible gelling copolymer with either a therapeutic agent in an aqueous solution containing the thermally reversible geling copolymer, and/or with a biodegradable polymer.

Advantages of the present invention include (1) the thermally reversible gel of the present invention exhibits a thermodynamic stability, and when geled, will not reverse to the liquid state upon dilution but may reverse to the liquid state only in response to a temperature change. Moreover, the thermally reversible gel of the present invention in a solution state has lower initial viscosity more suitable for tissue perfusion.

It is an object of the present invention to provide a therapeutic agent carrier.

It is a further object of the present invention to provide a method of making a therapeutic agent carrier.

It is a further object of the present invention to provide a biodegradable thermally reversible graft copolymer.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The present invention is a thermally reversible copolymer that is useful as a gel that forms without substantial syneresis when the thermally reversible copolymer is in an aqueous solution. Syneresis is defined as water expelled from a copolymer matrix upon gelation. Substantial syneresis is more than about 10 wt % water expelled from the copolymer matrix. According to the present invention, it is preferred that the syneresis be less than about 10 wt %, more preferably less than about 5 wt % and most preferably less than about 2 wt %. Substantially no syneresis is syneresis of less than about 2 wt %, preferably 0 wt %.

Figure 1:
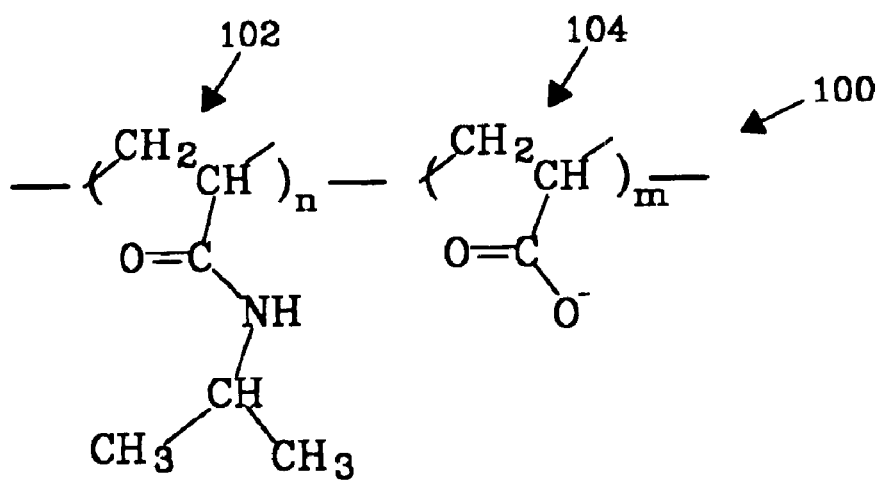
FIG. 1 is a depiction of a random copolymer of poly(N-isopropylacrylamide-co-acrylic acid) (NiPAAm/AAc), where n and m denote sequences of NiPAAm and AAc (respectively) that are of random length and are randomly distributed along the copolymer chain.

The thermally reversible copolymer is a linear random copolymer of an [meth-]acrylamide derivative and a hydrophilic comonomer wherein the linear random copolymer is in the form of a plurality of linear chains having a plurality of molecular weights greater than or equal to a minimum geling molecular weight cutoff. According to the present invention, the minimum geling molecular weight cutoff is at least several thousand and is preferably about 12,000. The presence of a substantial amount of copolymer or polymer chains having molecular weights less than the minimum geling molecular weight cutoff results in a milky solution that does not gel. Further, the amount of hydrophilic comonomer in the linear random copolymer is preferably less than about 10 mole %, more preferably less than about 5 mole % and most preferably about 2 mole %. When the hydrophyllic comonomer is AAc and the thermosensitive co-monomer is NiPAAm, the amount of AAc in the linear random copolymer is preferably from about 1 mole % to about 2.5 mole %, most preferably from about 1.6 mole % to about 1.9 mole %. The structure of linear chains is not cross linked. Moreover, the linear random copolymer structure is one in which a linear chain 100 is shared by randomly alternating portions of the [meth-]acrylamide derivative 102 and the hydrophilic comonomer 104 as depicted in FIG. 1.

The [meth-]acrylamide derivative is an N-alkyl substituted [meth-]acrylamide including but not limited to N-isopropyl[meth-]acrylamide, N,N-diethyl[meth-]acrylamide, N-[meth-]acryloylpyrrolidine, N-ethyl[meth-]acrylamide, and combinations thereof.

The hydrophilic comonomer is any hydrophilic comonomer that co-polymerizes with the [meth-]acrylamide derivative. Preferred hydrophilic comonomers are hydrophilic [meth-]acryl- compounds including but not limited to carboxylic acids, [meth-]acrylamide, hydrophilic [meth-]acrylamide derivatives, hydrophilic [meth-]acrylic acid esters. The carboxylic acid may be, for example, acrylic acid, methacrylic acid and combinations thereof. The hydrophilic acrylamide derivatives include but are not limited to N,N-diethyl[meth-]acrylamide, 2-[N,N-dimethylamino]

ethyl[meth-]acrylamide, 2-[N,N-diethylamino] ethyl[meth-]acrylamide, or combinations thereof. The hydrophilic [meth-]acrylic esters include but are not limited to 2-[N,N-diethylamino]ethyl[meth-]acrylate, 2-[N,N-dimethylamino]ethyl[meth-]acrylate, and combinations thereof.

According to the present invention, the thermally reversible polymer may be mixed with an aqueous solvent to form a thermally reversible geling solution or reversible geling solution. The aqueous solvent includes but is not limited to water and aqueous salt solutions. The salt solution is preferably a phosphate buffered saline solution for medical use.

The method of making the thermally reversible polymer according to the present invention has the steps of:
(a) mixing an [meth-]acrylamide derivative with a hydrophilic comonomer in a reaction solvent with an initiator forming a reaction mixture;
(b) polymerizing the reaction mixture and forming a first linear random copolymer having a plurality of linear chains having a plurality of molecular weights; and
(c) isolating and purifying the polymerized first linear random copolymer and obtaining a second linear random copolymer having a plurality of molecular weights greater than or equal to a minimum geling molecular weight cutoff.

The alternatives for the [meth-]acrylamide derivative and the hydrophilic comonomer have been set forth above and are not repeated here.

The reaction solvent may be aqueous or non-aqueous. The preferred aqueous solvent is simply water. Alternatively, the aqueous solvent is a salt solution. The non-aqueous solvent may be a hydrocarbon including but not limited to oxygenated hydrocarbon solvent, for example dioxane, chlorinated hydrocarbon solvent, for example chloroform, an aromatic hydrocarbon, for example benzene. Precipitation of the polymer occurs during polymerization in benzene. Dioxane is the preferred solvent because there is no precipitation during copolymerization thereby imparting greater uniformity of composition of the random copolymer (NiPAAM/AAc).

The amount of aqueous solvent with respect to [meth-]acrylamide derivative is preferably about 80 wt %, but may range from about 30 wt % to about 98 wt %. The amount of non-aqueous solvent with respect to the [meth-]acrylamide derivative is preferably about 80 wt % but may range from about 30 wt % to about 98 wt %.

The initiator may be any free radical initiator compatible with the [meth-]acrylamide derivative. The preferred initiator is 2,2'-azobis-isobutyrolnitrile (AIBN). The amount of the initiator with respect to the reaction mixture of solvent and polymer is preferably about 0.1 wt % but may range from about 0.01 wt % to about 2 wt %.

A reversible geling solution is made by mixing the thermally reversible polymer with an aqueous solution. The amount of aqueous solution with respect to polymer is from about 70 wt % to about 99 wt %, preferably about 98 wt % for NiPAAm/AAc to achieve a nonresorbable reversible gel with substantially no syneresis. The aqueous solution is preferably a salt solution.

In addition to the nonresorbable reversible gel composed of a linear random copolymer of N-isopropyl [meth-]acrylamide and [meth-]acrylic acid described in this invention, a biodegradable (resorbable) copolymer exhibiting similar gelation properties is obtained by grafting of the oligo [meth-]acrylamide derivative side chains on a biodegradable polymer of, e.g., polyaminoacids, poly(phosphasenes), poly(caprolaetone), polypeptides, polysaccharides and combinations thereof. Preferred oligo [meth-]acrylaniide derivative side chains include N-alkyl substituted [meth-]acrylamide derivatives, linear random copolymer of [meth-]acrylamide derivative and hydrophylic comonomer, and combinations thereof. Techniques of grafting of oligo-N-isopropyl [meth]acrylamide side chains on a nonbiodegradable pH-sensitive homopolymer are described (Chen and Hoffman). The technique(s) of Chen an Hoffman were use herein to graft the oligo-N-isopropyl[meth] acrylamide side chains on alternative biodegradable polymers such as polyaminoacids, poly(phosphasenes), poly(caprolactone), polypeptides, polysaccharides and combinations thereof. The first step of the synthesis is either the free radical homopolymerization or the random copolymerization of the oligo-N-isopropyl[meth-]acrylamide side chains by free radical polymerization using an aminoterminated chain transfer agent, for example 2-aminoethanethiol hydrochloride. The next step is the coupling of the amino-terminated macromer to the carboxyl moieties of the biodegradable polymer using the activation reagent, e.g., dicyclohexyl carbodiimide. Other biodegradable polymers such as poly(phosphazenes) poly(caprolactone), polypeptides, polysaccharides and combinations thereof may also be grafted with the oligo-N-isopropyl[meth-]acrylamide side chains using similar synthetic techniques.

The resorbable and/or non-resorbable thermally reversible gel(s) of the present invention is/are useful as a therapeutic agent carrier. Therapeutic agent is a biologically active agent including but not limited to anti-cancer agents, hormones, antibiotics, narcotic antagonists, analgesics, anti-inflammatory agents, anti-depressant, anti-epileptic, anti-malarial agents, immunoactivators, growth factors, gene therapy agents, oligonucleotides, therapeutic peptides and proteins, and combinations thereof. More specifically, it is useful as a chemo-embolic material by combining the reversible copolymer with a chemo-therapeutic agent (CTA). At body temperature the reversible copolymer-CTA combination forms a reversible gel matrix containing the entrapped CTA, whereas at room temperature the reversible copolymer-CTA combination is a free-flowing (injectable) solution. The advantages of reversible gels as chemo-embolizing agents include: fast and effective embolization due to the immediate gel formation at body temperature, and easy incorporation of drugs either by simple mixing with copolymer solution wherein the drug or therapeutic agent is not covalently bonded to the reversible copolymer or by covalently bonding the drug or therapeutic agent to the reversible copolymer. The localized and controlled release of the CTA entrapped within the gel matrix enhances the efficacy and decreases the systemic toxic effects of chemotherapy.

EXAMPLE 1

An experiment was conducted to demonstrate synthesis and thermoreversible gel formation of poly(N-isopropylacrylamide -co-acrylic acid) (NiPAAm/AAc). The linear high molecular weight NiPAAm/AAc copolymers containing different amounts of AAc were synthesized by a free radical copolymerization.

The [meth-]acrylamide derivative was N-isopropylacrylamide (NiPAAm) (Fisher, Co.) that was recrystallized from hexane before use. The initiator 2,2'-azobis -isobutyronitrile (AIBN) (Eastman Kodak, Co.) was recrystallized from methanol. The hydrophilic comonomer was acrylic acid (AAc) (Aldrich Co.) that was purified before use by vacuum distillation at 39° C./10 mm Hg. The reaction solvent, dioxane, HPLC grade (Aldrich Co.) was used as received. The mixture of [meth-]acrylamide derivative, initiator, hydrophilic comonomer, and solvent formed the reaction mixture.

The molar feed ratio of NiPAAm to AAc was varied as 99:1, 98:2 and 97:3. The copolymerization was carried out in dioxane (80 wt %), with the amount of AIBN initiator of $1.219 \times 10^{-3}$ mols/L. The reaction proceeded at 60° C. for 18 hours. The resulting copolymer solution was diluted with fresh dioxane and added dropwise to a ten-fold excess of diethyl ether producing copolymer precipitation. The precipitated copolymer was isolated by filtration and drying. The isolated copolymer was redissolved in acetone and reprecipitated into ten-fold excess diethyl ether. The final, essential step of purification involved dialysis of aqueous copolymer solution through 12,000–14,000 molecular weight cut off (MWCO) dialysis membrane. Dialysis removed the residual unreacted monomer and all copolymer fractions with molecular weights smaller than the MWCO of the dialysis membrane, resulting in a purified copolymer product. The purified copolymer product was further freeze dried.

The removal of molecular weights below 12,000 from the synthesized copolymers was confirmed by gel permeation chromatography. The removal of unreacted monomers was confirmed by nuclear magnetic resonance.

The lower critical solution temperature (LCST) of the synthesized copolymers was evaluated by the cloud point determination method. In this method, 1 wt. % solutions of synthesized copolymers in phosphate buffered saline were heated from 20 to 50° C. in 2-deg increments every 10 min. and the absorbance at 450 nm was measured. The cloud point, corresponding to the LCST was determined as the temperature at the inflection point in the absorbance versus temperature curve. NiPAAm homopolymer exhibited an LCST at 32° C. Copolymerization with hydrophilic comonomers shifted the LCST to the physiological temperature range of 36-38° C. NiPAAm/AAc copolymer containing 2 mol % of AAc exhibited the LCST at 37° C.

Figure 2:
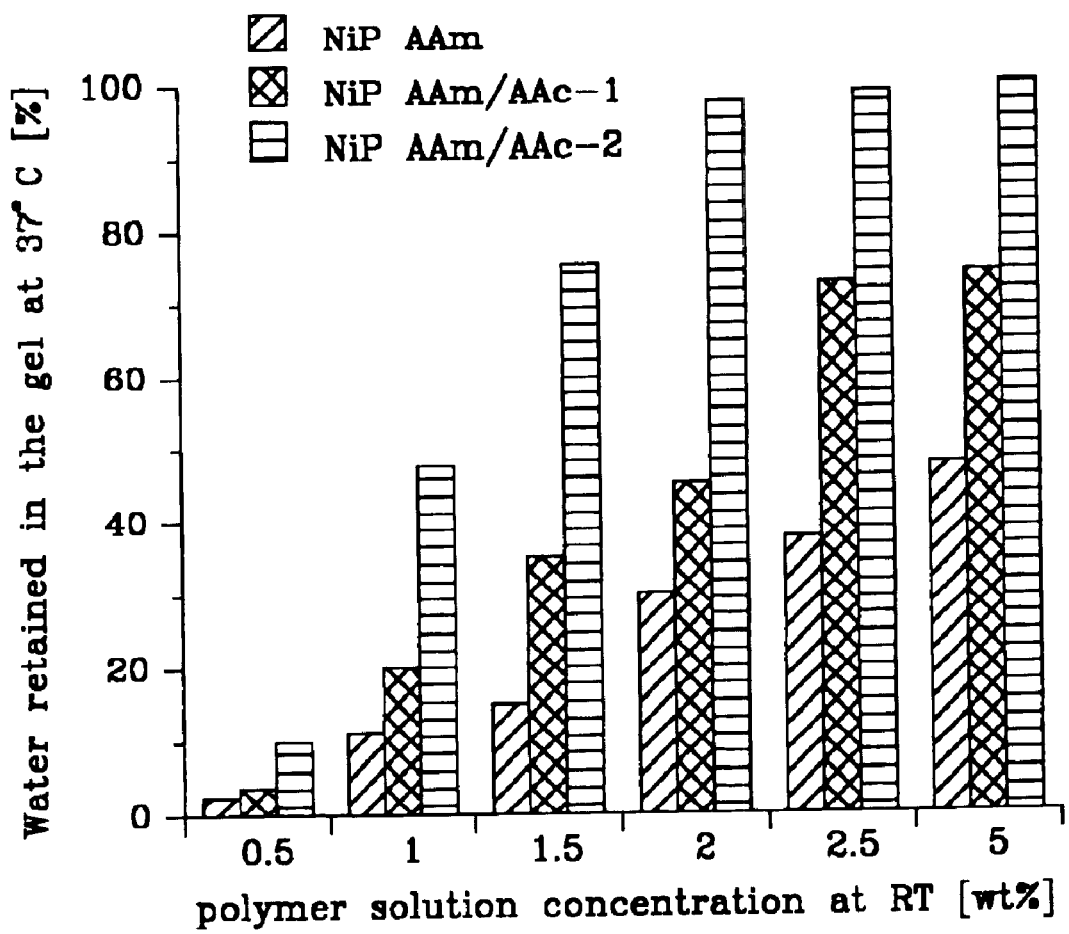
FIG. 2 is a bar graph of water retention in the gel versus initial copolymer concentration in the geling solution.

Thermally reversible gel formation was studied at 37° C. The freeze-dried copolymer was dissolved in phosphate buffered saline (PBS) at different copolymer concentrations (0.5, 1.0, 1.5, 2.0, 2.5, and 5.0 wt %) forming copolymer solutions. The PBS was specifically 0.15 M NaCl, 0.01 M phosphates $KH_2PO_4$, and $Na_2HPO_4$. The copolymer solutions were thermally equilibrated at 37° C. for 24 hours. The syneresis (amount of water expelled from the gel) was measured gravimetrically. Syneresis of thermoreversible hydrogels of N-isopropylacrylamide (NiPAAm) and its copolymers with acrylic acid (AAc) was affected by copolymer composition (0, 1, 2 mol % of AAc) and polymer concentration as shown in FIG. 2. In FIG. 2 the amount of water retained in the gel is plotted as a function of the initial copolymer concentration in solution (before geling). It was unexpectedly discovered that the solution containing at least about 2 wt % of the NiPAAm/AAc copolymer having at least about 2.0 mol % of AAc was able to produce a reversible gel exhibiting substantially no syneresis.

EXAMPLE 2

An experiment was conducted to confirm the necessity of the minimum geling molecular weight cutoff. A geling polymer solution was made as in Example 1, but the solution was not dialyzed so that no low molecular weight species were removed. The result was a solution, milky in appearance, that did not form a gel.

EXAMPLE 3

An experiment (release study) was conducted to demonstrate that the reversible gel would release a therapeutic agent at a controlled rate.

Figure 3:
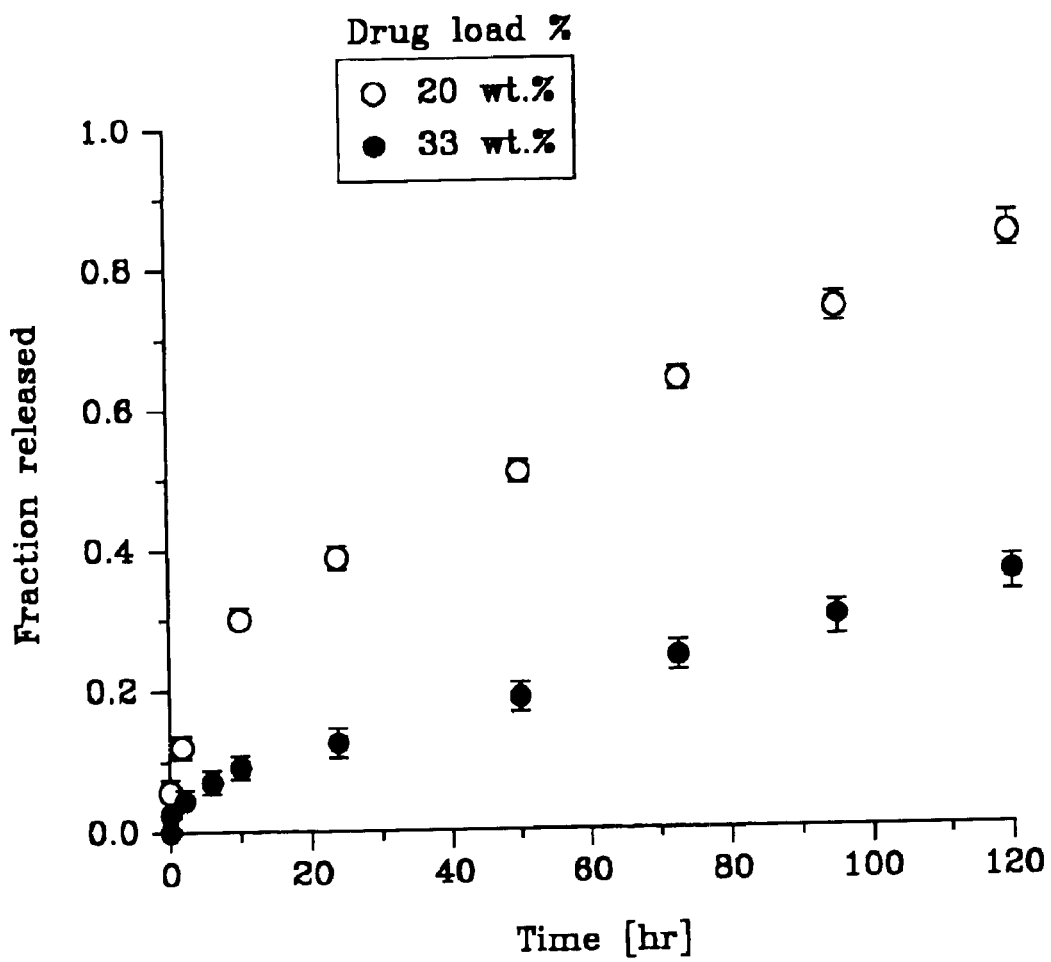
FIG. 3 is a graph of fraction of 5-fluorouracil (5FU) released versus time from NiPAAm/AAc copolymer with two different drug loading percentages (20 and 33 wt % of 5FU).

The release study was conducted using NiPAAm/AAc-2 copolymer containing 2 mol % of acrylic acid. Suspensions containing 20 and 33.3 wt % of 5-fluorouracil (5FU) in 5 wt. % copolymer solutions in PBS were prepared at room temperature by mixing and brief sonication. In all suspensions, the 5FU was physically mixed in the suspensions but was not covalently bonded to the copolymer. A 1 ml amount of copolymer/drug suspension was injected into a small dialysis tubing, (d=25 mm and MWCO 12,000–14,000). During the injection, the dialysis tubing was immersed in PBS equilibrated at 37° C. Instantaneous gel formation was observed inside the dialysis tubing. The tubing was then sealed and a gentle mixing of the outside solution was turned on. Samples of the outside solution were taken at predetermined time intervals and replaced with the same amount of fresh PBS buffer. Concentration of 5FU was analyzed by UV spectrometry at 266 nm. The release profiles of 5FU from NiPAAm/AAc-2 copolymer are shown in FIG. 3, where fraction of the released drug is plotted as a function of time.

The release from gels containing 20 and 33 wt. % of drug were investigated. The release profiles differed markedly in terms of the observed initial burst effect. Within the firs 24 hr., the gel containing 20 wt. % of 5FU released almost 40% of drug, whereas the gel containing 33 wt. % of 5FU released less than 15% of drug. Usually, in the case of drug release from a highly hydrated copolymer matrix the initial release rate is greater for the gels with higher drug loading. To explain this apparent contradiction with the expected results we have to consider the substantial syneresis exhibited by the gel containing 20 wt. % of drug. In this case, the initial burst effect, normally caused by a fast diffusion from the outer gel layer, was enhanced by the amount of drug expelled from the gel matrix due to the syneresis. After 24 hr., i.e., after the initial burst effect, a constant release rate was observed for 120 hr for both gels, with a higher release rate observed for the gel containing 20 wt. % loading of 5FU.

EXAMPLE 4

A further experiment was conducted to demonstrate the behavior of the gel during tissue perfusion in lymph nodes. A freeze dried copolymer of N-isopropylacrylamide with acrylic acid (2 mol %) NiPAAm/AAc)] was dissolved in PBS as in Example 1. A dye Naphthol blue-black, electrophoresis reagent, from Sigma was added to the copolymer solution. In all solutions, the dye was physically mixed by dissolving into the solutions, but was not covalently bonded to the copolymer.

Canine lymph nodes were freshly isolated and equilibrated at 37° C. PBS for 30 min.

Figure 4A:
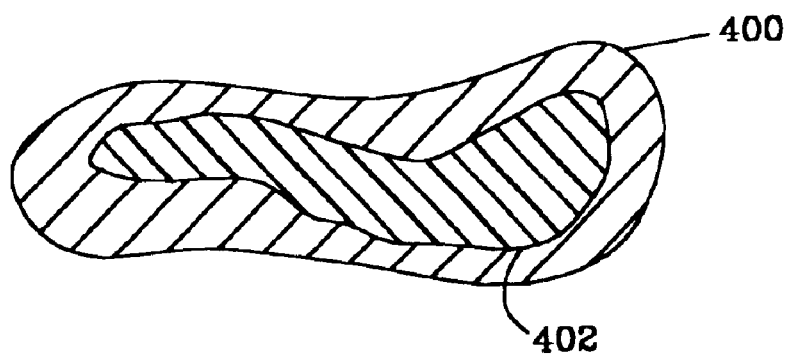
FIG. 4*a* depicts a lymph node sectioned after the injection of thermally reversible copolymer/dye solution.

A 5 wt % solution of NiPAAm/AAc in PBS, containing also a small amount (>0.01%) of the blue dye was prepared and cooled in an ice bath. Small aliquouts (0.2–0.3 ml) of the cold polymer solution were injected into the freshly isolated canine lymph nodes. After the injection, lymph nodes were kept at 37° C. PBS for 10–15 min permitting the thermal gelation of the injected copolymer solution. The injected lymph nodes were then cut open with a razor blade to evaluate the extent of tissue perfusion. As shown in FIG. 4a, the dye perfusion within the lymph node 400 was limited to the extent of perfusion of the geled copolymer solution 402, and was clearly visible.

Figure 4B:
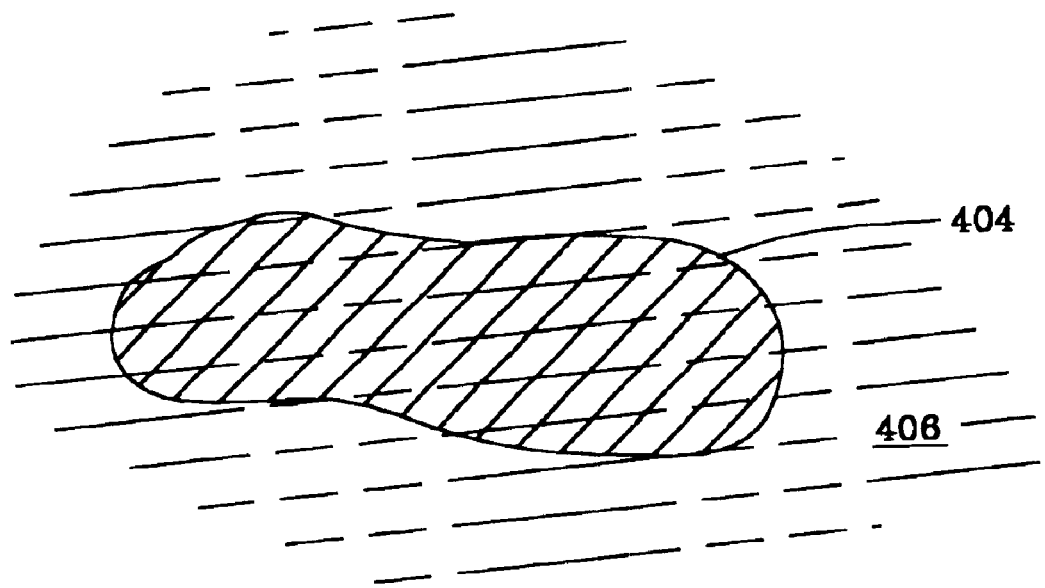
FIG. 4*b* depicts another lymph node sectioned after the injection of the dye solution alone.

As a control, dye solution in PBS only was injected into another lymph node 404 without mixing the dye into the geling solution. Dye 406 was not contained locally within the lymph node but diffused throughout and beyond the lymph node as illustrated in FIG. 4b. Injection of the dye solution alone resulted in no dye localization within the lymph node 404.

EXAMPLE 5

The polymerization was conducted as described in the Example 1 but using a different molar feed ratio of comonomers. The molar feed ratio of NiPAAm to AAc was varied as 98.4:1.6, 98.2:1.8, 98.1:1.9 and 98.0:2.0. Gelation temperature was measured for 5 wt % copolymer solutions in PBS, as described in Example 1. Gelation temperatures are listed in Table E5-1.

TABLE E5-1

Gelation temperature as a function of molar feed ratio

| Molar feed ratio NiPAAm:AAc | Gelation temperature [° C.] |
|---|---|
| 98.4:1.6 | 34.0 ± 0.1 |
| 98.2:1.8 | 35.5 ± 0.1 |
| 98.1:1.9 | 36.5 ± 0.1 |
| 98.0:2.0 | 37.4 ± 0.1 |

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A biodegradable thermally reversible graft copolymer, comprising:
   a. a biodegradable, resorbable polymer; grafted with
   b. a side chain selected from the group consisting of homo-oligomers of [meth-]acrylamide derivatives and co-oligomers of [meth-]acrylamide derivatives copolymerized with hydrophilic comonomers
   c. said biodegradable thermally reversible graft copolymer forming a reversible gel.

2. The copolymer as recited in claim 1, wherein said biodegradable copolymer is selected from the group consisting of polyaminoacids, poly(phosphazenes). poly (caprolactone), polypeptides, polysaccharides and combination thereof.

3. The copolymer as recited in claim 1, wherein said oligo [meth-]acrylamide derivative is an N-alkyl substituted [meth-]aciylaimde derivative.

4. The copolymer as recited in claim 1, wherein said oligo [meth-]acrylamide derivative side chain is randomly copolymerized with a hydrophilic comonomer as a linear random oligomer, said linear random oligomer having molecular weight less than a minimum geling molecular weight cutoff.

5. A reversible geling copolymer solution, comprising the copolymer as recited in claim 1, mixed with an aqueous solvent.

6. A therapeutic agent carrier, comprising:
   the copolymer solution as recited in claim 5, mixed with a therapeutic agent.

* * * * *